(12) United States Patent
Busoni

(10) Patent No.: US 11,351,367 B2
(45) Date of Patent: Jun. 7, 2022

(54) DEVICE FOR STIMULATING SKIN REGENERATION

(71) Applicant: Maurizio Busoni, Florence (IT)

(72) Inventor: Maurizio Busoni, Florence (IT)

( * ) Notice: Subject to any disclaimer, the term of this patent is extended or adjusted under 35 U.S.C. 154(b) by 0 days.

(21) Appl. No.: 16/646,427

(22) PCT Filed: Sep. 11, 2018

(86) PCT No.: PCT/IB2018/056932
§ 371 (c)(1),
(2) Date: Mar. 11, 2020

(87) PCT Pub. No.: WO2019/049105
PCT Pub. Date: Mar. 14, 2019

(65) Prior Publication Data
US 2020/0282212 A1     Sep. 10, 2020

(30) Foreign Application Priority Data

Sep. 11, 2017   (IT) .................. 102017000101375

(51) Int. Cl.
*A61N 1/32*       (2006.01)
*A61N 1/36*       (2006.01)
(Continued)

(52) U.S. Cl.
CPC ........... *A61N 1/328* (2013.01); *A61N 1/0464* (2013.01); *A61N 1/326* (2013.01); *A61N 1/36014* (2013.01); *A61N 1/40* (2013.01)

(58) Field of Classification Search
CPC .. A61N 1/40; A61N 1/36031; A61N 1/36014; A61N 1/328; A61N 1/326; A61N 1/0476; A61N 1/0464; A61H 2201/1238; A61H 2201/10; A61H 2201/0153; A61H 2201/013; A61H 39/002; A61H 9/0057; A61B 2018/00291; A61B 2018/00452;
(Continued)

(56) References Cited

U.S. PATENT DOCUMENTS

| 2005/0251118 A1* | 11/2005 | Anderson | A61B 18/203 606/9 |
| 2010/0210993 A1 | 8/2010 | Lion et al. | |
| 2011/0112520 A1* | 5/2011 | Michael | A61N 1/0412 606/13 |

FOREIGN PATENT DOCUMENTS

| WO | 2003/079916 A1 | 10/2003 | |
| WO | WO-2007096009 A1 * | 8/2007 | ............. A61N 1/403 |

OTHER PUBLICATIONS

International Search Report and Written Opinion for corresponding Application No. PCT/IB2018/056932 (dated Dec. 13, 2018).
(Continued)

*Primary Examiner* — Carl H Layno
*Assistant Examiner* — Anh-Khoa N Dinh
(74) *Attorney, Agent, or Firm* — Troutman Pepper Hamilton Sanders LLP (Rochester)

(57) ABSTRACT

A device and a method for stimulating skin regeneration is described which allows exploiting the combined action of the surface vasculature (given by the action of the vacuum) and of the cellular regeneration (given by the electromagnetic field generated by a capacitive system) combined with the skin electrostimulation applied, in this case, so as to amplify the biological effect of the electromagnetic field.

10 Claims, 4 Drawing Sheets

(51) Int. Cl.
*A61N 1/40* (2006.01)
*A61N 1/04* (2006.01)

(58) Field of Classification Search
CPC ... A61B 18/14; A61B 18/4836; A61B 5/0531; A61B 5/442
See application file for complete search history.

(56) References Cited

OTHER PUBLICATIONS

Kreindel and Mulholland, "The Basic Science of Radiofrequency-Based Devices," Enhanced Liposuction, pp. 1-25 (2021).

* cited by examiner

DEVICE FOR STIMULATING SKIN REGENERATION

This application is a national stage application under 35 U.S.C. § 371 of PCT Application No. PCT/IB2018/056932, filed Sep. 11, 2018, which claims priority benefit of Italy Application No. 102017000101375, filed Sep. 11, 2017, which are hereby incorporated by reference in their entirety.

TECHNICAL FIELD

The present invention relates to the field of devices and methods for stimulating skin repair and regeneration.

PRIOR ART

The aging of the skin is the sum of chronoaging phenomena, or the passing of time, and of photoaging, or the consequence of exposure to the environment, and therefore ultraviolet, smog, etc.

These phenomena lead to known consequences, summarized with an extremely simple concept: our skin is no longer able to reproduce all the cells and molecules that decay both as a consequence of apoptosis and due to wrong lifestyles.

A regenerative deficit follows, where skin aging increases substantially and apparently day after day, leaving the skin increasingly emptied, less elastic and less hydrated. This regenerative deficit can also manifest itself as a result of traumas and injuries (abrasions, post-surgical scars, acne, burns) or aesthetic pathologies such as cellulitis and stretch marks.

Over the last 20 years, aesthetic medicine has proposed different methods to slow down the phenomenon of skin aging, or to increase the regenerative phenomena.

Many methods are explicitly based on the philosophy of damage, others on the use of topical cosmetics, others on more or less deep peels, others on systems for the delivery of active ingredients, others on injective therapies (fillers and revitalizers).

All the proposed methods offer a transitory improvement, on the understanding that they are based on a permanent damage that varies from simple fibrosis induced by the penetration of a needle, up to the denaturation of the existing collagen, in fact creating a further skin aging in the medium term.

The interest to be able to attenuate the phenomena of chronoaging and of photoaging, as well as the consequences of traumas and lesions or aesthetic pathologies without however creating a further damage, but directly pursuing the regeneration of the skin, is therefore evident.

In the field of sports medicine and rehabilitative therapy, the ability of electromagnetic fields, generated with a capacitive radiofrequency, to promote the regeneration of muscle fiber is appreciated.

It is also known that the muscle fiber is much more vascularized than the skin and the blood that flows through it is much more oxygenated and rich in electrolytes, already present in the muscles in high percentage as they represent the elements that allow the interpenetration of actin fibers with those of myosin, as they are essential elements to achieve muscle contraction.

Precisely for this reason, the muscle, in its normal condition, is an electrical and therefore electromagnetic conductor better than the skin.

It follows that the regeneration obtained with respect to the muscle fiber is not currently replicable to the same extent with the skin tissue, since the lower electrical conductivity proportionally attenuates the oscillatory motion induced by the electromagnetic field towards the treated tissue.

The object of the present invention is to improve the electric and electromagnetic conductivity of the skin tissue, so that a regeneration compatible with that which characterizes the muscle fiber treated with electromagnetic fields may be achieved.

U.S. documents 01/0112520 and WO03/079916 describe an apparatus for treating the skin under the combined action of vacuum and radio frequencies, there is no mention of electrostimulation. Moreover, the apparatuses described in the aforesaid documents supply only resistive coupling radiofrequency, or resistive radiofrequency, as shown by the total absence of shielding on the surface of the RF electrodes described in the cited documents, and the total absence of references to capacitive radiofrequency or capacitive coupling or to the capacitive effect in general, in these documents. No mention is made to electrostimulation.

Document WO2007/096009 (on behalf of the same Applicant) similarly describes a device for treating the striae of the skin through the simultaneous application of a massage and warming action of the skin, also in this case there is no mention of electrostimulation.

SUMMARY OF THE INVENTION

A device for stimulating skin regeneration is described which allows exploiting the combined action of the surface vasculature (given for example by the possible application of the vacuum and/or by the skin stimulation of the part to be treated), of cellular regeneration (given for example by the application of an electromagnetic field generated with a capacitive system) and electrical stimulation of the skin. The use of skin electrostimulation, together with the application of capacitive coupling radiofrequency, also allows an evident amplification of the effectiveness of the electromagnetic field generated by the capacitive coupling radiofrequency. This electrostimulation, in fact, conveys an additional amount of electrons on the treated biological tissue, crossing the patient's skin and reducing the electrical resistance thereof. Being the effective dose of the electromagnetic field administered inversely proportional to the electrical resistance of the patient's skin, lowering the resistance of the treated biological tissue amplifies the effectiveness of the electromagnetic field.

BRIEF DESCRIPTION OF THE FIGURES

Further features and advantages of the present invention will become more apparent from the following detailed description, given by way of a non-limiting example and shown in the accompanying figures, in which.

Figure 1:
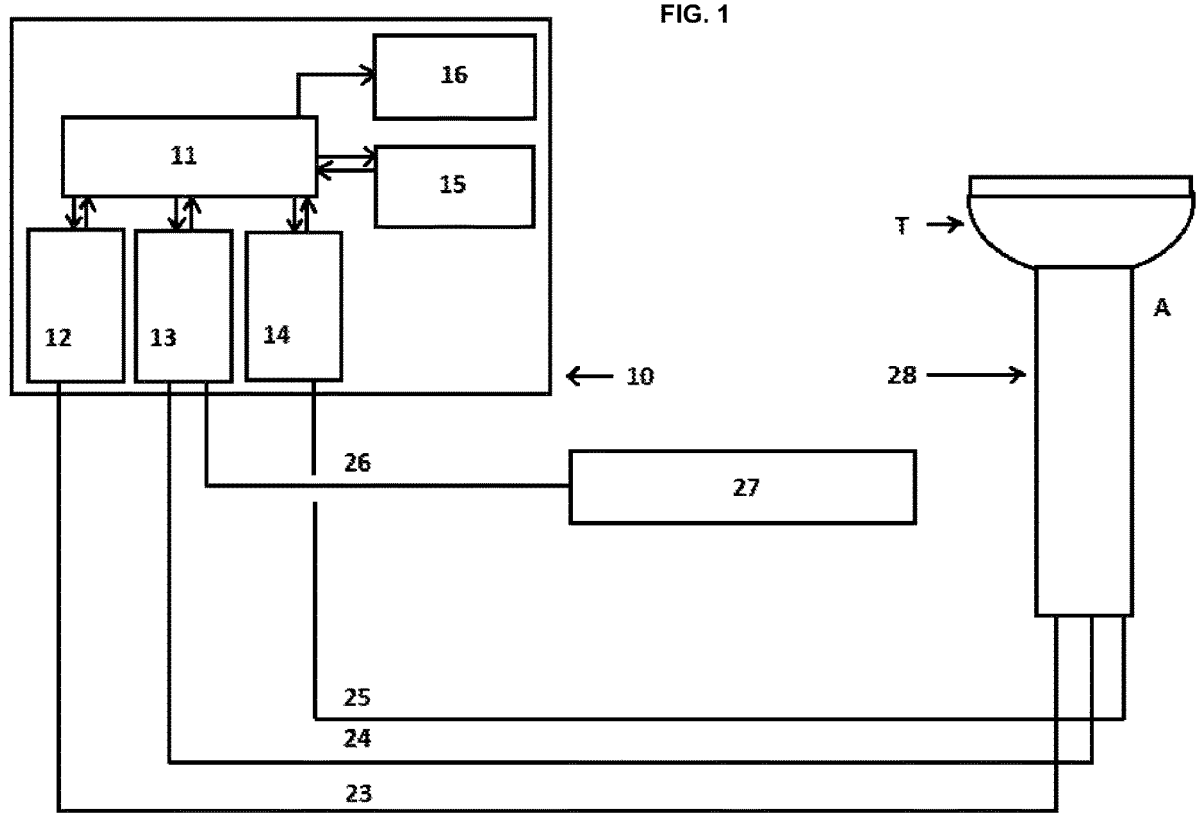
FIG. 1 schematically shows a preferred embodiment of the device according to the present invention.

The component parts of the apparatus according to the present description are represented in the drawings, where appropriate, with conventional symbols, showing only those specific details which are pertinent to the understanding of the embodiments of the present invention, so as not to highlight details which will be immediately evident, to the man skilled in the art, with reference to the description given herein.

DETAILED DESCRIPTION OF THE INVENTION

The present invention allows overcoming the above problems with a device which allows exploiting the combined action of the surface vascularization, given for example by the action of the vacuum, and of the cellular regeneration given by the electromagnetic field generated with a capacitive system, combined with skin electrostimulation.

As can be seen in FIG. 1, a preferred embodiment of the device 10 according to the invention comprises:
- a logic unit 11;
- a vacuum generation system 12;
- a capacitive system 13;
- an electrical stimulation system 14;
- a handpiece A;
- a reference handpiece 27 to be held by the patient.

Figure 4:
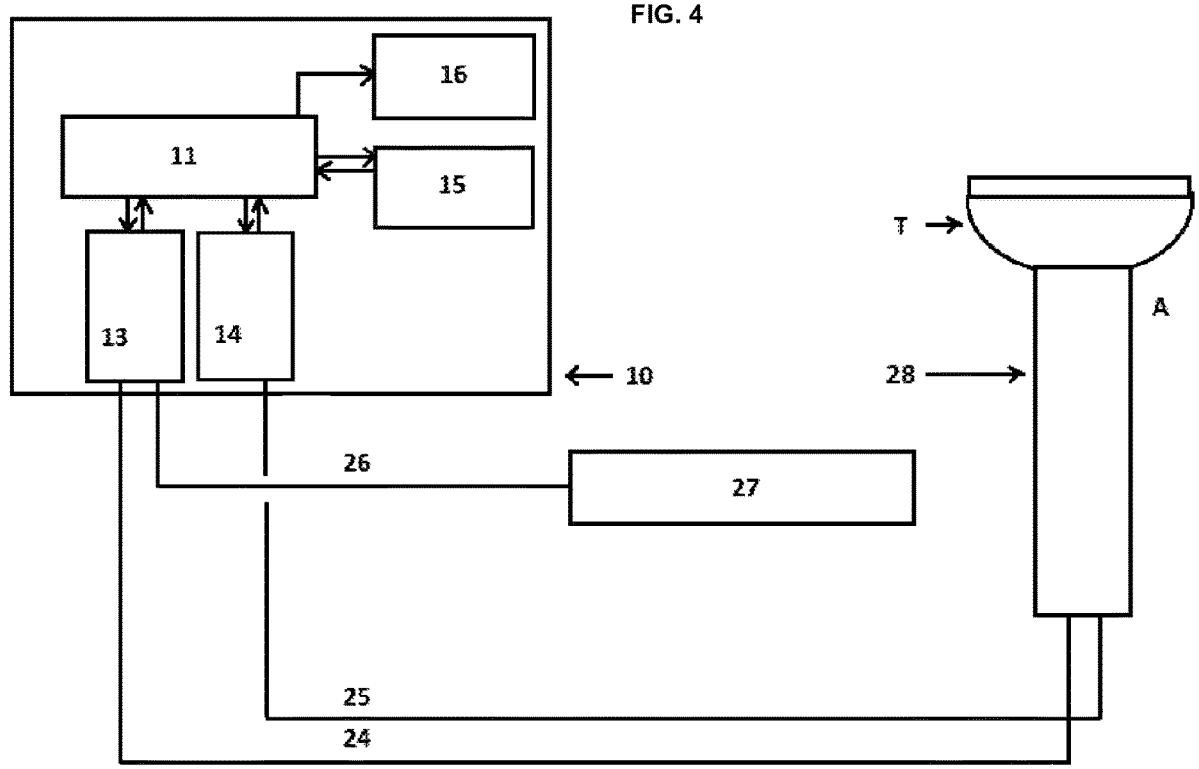
FIG. 4 schematically shows another preferred embodiment of the device according to the present invention.

With reference to the accompanying FIG. 4, another preferred embodiment of the device 10 according to the invention comprises:
- a logic unit 11;
- a capacitive system 13;
- an electrical stimulation system 14;
- a handpiece A;
- a reference handpiece 27 to be held by the patient.

By logic unit 11 it is meant a printed circuit provided with a microprocessor capable of managing all the power parts, determining their intensity, frequency, nature and timing, normally it is provided with keyboard 15 and a display 16 for the necessary interventions by the operator.

The logic unit 11 manages and regulates the possible generation of vacuum, the capacitive system and the electrical stimulation.

The vacuum generation system 12 refers to a vacuum pump, or other device capable of creating the vacuum, which is then preferably supplied by means of a battery of solenoid valves or another method suitable for varying the negative pressure thereof, preferably connected to system for reading the actual vacuum produced.

The capacitive system 13 consists of an electronic circuit comprising an AC power supply connected to one or more shielded electrodes 19, by means of a shielded cable 24, and to a reference handpiece 27, through a monopolar cable 26; the system generates a signal with a frequency ranging from 0.3 to 10 MHz and preferably from 0.3 to 1.5 MHz.

The electrical stimulation system 14 consists of an electronic circuit comprising an electrostimulation generator which produces direct current and various types of square waves and half-waves with determined polarity, connected to the pairs of electrodes 21 placed on the head of the handpiece via a shielded multipolar cable 25.

The handpiece A comprises:
- a grip 28;
- a head T;
- one or more shielded electrodes 19 for supplying the capacitive system, placed on the inner surface and/or on the edge of the head T and however coated by a dielectric 20;
- one or more pairs of electrodes 21 for delivering an electrical stimulation, arranged on the inner surface and/or on the edge of the head T so that the two electrodes of each pair are diametrically opposed to each other;
- possibly a cavity 22 for the vacuum application.

The shielded electrodes 19 consist of two distinct parts: the electrode as such, consisting of an excellent electrical conductor (generally metal) and a dielectric coating layer 20 intended to come into contact with the patient's skin.

Figure 2:
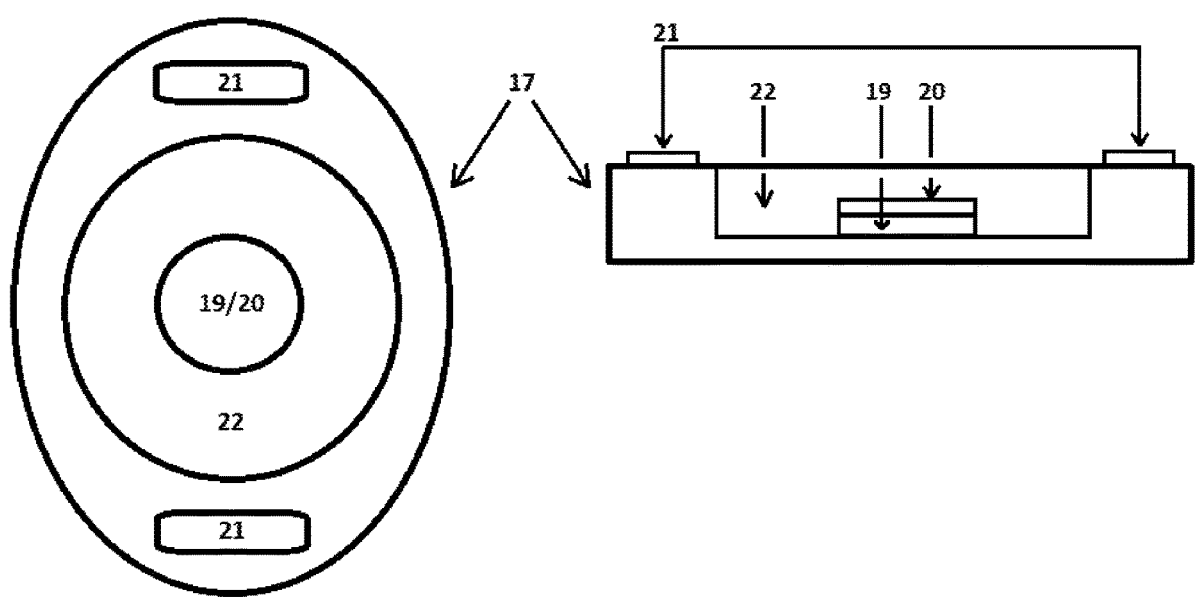
FIG. 2 schematically shows the head (i.e. the terminal part that comes into contact with the skin) of a concave-surface handpiece.
Figure 3:
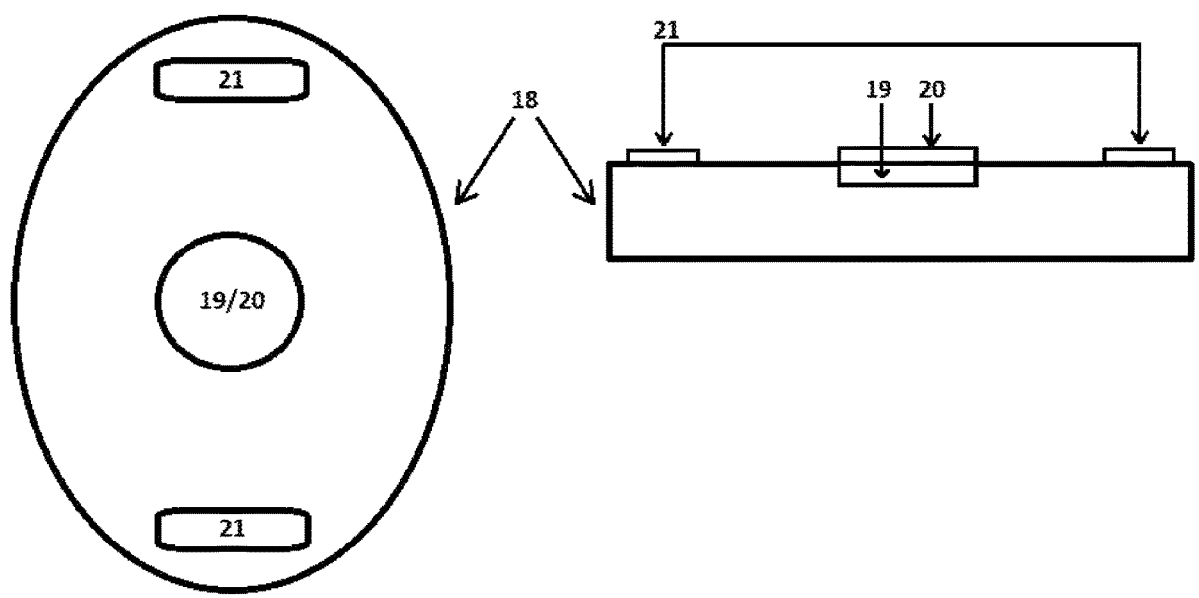
FIG. 3 schematically shows the head (i.e., the terminal part that comes into contact with the skin) of an alternative flat-surface handpiece.

The head T may be a concave surface (17 as shown in FIG. 2) or a flat surface (18, see FIG. 3) and is connected:
- to the capacitive generator 13 with a shielded coaxial cable 24 (for example type RG58 MIL);
- to the electrical stimulation generator 14 (with a shielded multipolar cable 25);
- to the vacuum generator 12 (with a pneumatic cable 23).

The concave surface handpiece 17 has a shape such as to allow a good vacuum tightness, due to an introflected part which may have various shapes and dimensions, such as to create a cavity 22 capable of ensuring a good vacuum seal.

The flat-surface handpiece 18 is instead used for the delivery of capacitive 13 and electrical stimulation generators, with or without the action of the vacuum.

The reference handpiece 27 to be held by the patient consists of a metal body or another very good electrical conductor and is connected to the capacitive generator 13 by means of a monopolar cable 26.

The cables 23, 24, 25 and 26 may be mechanically connected to each other or remain separate.

The device 10 is therefore capable of generating (simultaneously or separately) the vacuum effect, a capacitive signal and an electric stimulation.

If preferred, the device 10 may be provided with a timer which allows the automatic deactivation thereof after a certain time.

The device 10 obviously includes the normal internal circuitry, both electric and pneumatic, and the connection to the mains or battery supply.

The device 10 provides both the possibility that the generators of the vacuum 12, of the capacitive system 13 and of the electrostimulation 14 are received in a single structure, and that the generators themselves consist of independent units and are then connected on a single handpiece of any shape or that are delivered simultaneously on the same patient through different handpieces.

If required, the device according to the invention may be provided with the following complementary devices.

Devices provided with an abrasive surface capable of performing an effective peeling, connected to the vacuum generator 12 by means of a pneumatic cable 23 or a different parallel cable.

Plates of different sizes and shapes designed to deliver hot and cold through the use of resistors or infrared heat generators or Peltier cells for combined heat/cold management or other equivalent technology.

Handpieces or plates of different sizes and shapes, adapted to deliver ultrasounds at different frequencies and intensities, whether traditional or focused, with continuous or pulsed emission.

Handpieces or plates of different sizes and shapes, adapted to deliver polarized and non-polarized light, both by LED and other equivalent technology.

The use of the device according to the invention is clear per se.

After setting the values necessary for the treatment and activating the device, the head of the handpiece A is passed directly over the skin surface of the patient.

The device 10 generates a high frequency alternating current which is applied to the skin through the shielded electrode 19, coated with the dielectric 20, while the treated patient grips the reference handpiece 27 designed to close the electromagnetic circuit and read the bio-feedback.

The treatment is continued until the treated skin is slightly reddened, brighter and slightly warmer than the surrounding tissue.

As will be understood, the shielded electrode 19 and the reference handpiece 27 act like the plates of a capacitor, where the dielectric 20 and the horny layer of the treated skin form the capacitor dielectric. When current is supplied, charges are established on the shielded electrode 19, coated with the dielectric 20, which are rapidly alternated, thus causing an electromagnetic field within the biological tissue which, just as rapidly, changes direction and generates heat. The treated tissues are partly assimilated to a dielectric (horny layer consisting of denucleated cells) and partly assimilated to electrical conductors (dermis). Inside the electric conductors and through said dielectric there occurs the action of the electromagnetic field.

Once the logic unit 11 determines the optimal tuning between the capacitive generator 13 and the tissue to be treated, the device starts to deliver the electrical stimulation through the pairs of electrodes 21.

Due to this position, the skin tissue involved in the lines of force of the electromagnetic field will also be impinged by the migration of electrons and the consequent bidirectional flow of ions of the treated skin, which will contribute to improve the electrical conductivity of the tissue and consequently proportionally improve the effectiveness of the electromagnetic field.

Stimulation can occur with an alternating signal, with a continuous polarized signal or with a polarity inversion signal.

The function of electrical stimulation is simple: to allow the electromagnetic field to pass through a flow of electrons which causes an orderly movement of electrical charges within the skin tissue.

All this allows a greater ionic motility within the biological tissue and favors a reduction of the electrical resistance, i.e. it increases the electrical and electromagnetic conductivity, therefore the electromagnetic field moves with greater speed, proportional to the better conductivity of the tissue, or to its lower electrical resistance.

Another effect given by the better propagation of the electromagnetic field will be a rapid overheating of the skin tissue, whose temperature stabilizes between 39° and 40° C., that is, at the point of maximum regenerative potential, as documented by the Law of Van't Hoff, which has demonstrated a cell reproduction greater than 300% in this thermal range.

The synergistic action of vacuum, intended to promote good vascular gymnastics and therefore a greater supply of blood into the skin, with the consequent release of oxygen and nutritional elements, is facilitated by the stabilization of the temperature between 39° and 40° C., which reduces the viscosity of blood and allows a superior yield of the pumping action.

All this leads to an increase in skin regeneration, very similar to the regenerative faculty of muscles treated with electromagnetic fields, as documented by decades of scientific publications.

Using an integrated reading platform developed by NXP Semiconductors, part of the Philips group, on which a "Bio-feed-back" application was developed, the sliding speed of the electromagnetic wave generated by the device covered by the patent WO2007/096009 on the skin tissue treated with that obtained with the present device was compared.

The average effective value found was between 300 and 450 mV for the device described in WO2007/096009.

Applying, on the same tissue, at the same time, an electrical stimulation as indicated in the present invention, by positioning one or more pairs of electrodes on the edge of the handpiece, an average effective value of between 700 and 800 mV was found.

Since the electric current velocity is inversely proportional to the electrical resistance of the conductor, the present invention achieves the predetermined result, i.e. a strong pro tempore reduction of the electrical resistance of the skin tissue, bringing it closer to the specifications of the muscle fiber.

The lower electrical resistance therefore allows, with the same dispensing time and delivered intensity, a greater efficacy of the electromagnetic field on the skin tissue, given by the greater dose that is biologically active.

The increase in the voltage of the electromagnetic field up to 700/800 mV results in a greater push towards sodium and potassium ions, which will result in faster crossing of the cell membranes—whose "membrane potential" is notoriously comprised between 50 and 70 mV—and thus achieve greater skin regeneration, similar to the maximum potential regeneration that for decades has characterized the application of electromagnetic fields to muscle fibers.

It should be noted that the device is extremely easy to use and that the logic unit intervenes by automatically varying its parameters set according to the reading of the feedback signal which allows evaluating the actual effectiveness of the energy produced and applied on the skin tissue of the patient.

The invention claimed is:

1. A device for stimulating skin regeneration which allows the simultaneous action of applying, to a patient's skin, an electromagnetic field generated with a radiofrequency (RF) capacitive system and skin electrostimulation, said device comprising:
    a RF capacitive system consisting of an electronic circuit comprising an alternating current power supply capable of generating a signal with a varying frequency from 0.3 to 10 MHz, connected to a reference handpiece to be held by the patient and connected to one or more shielded electrodes for delivering to the patient's skin the electromagnetic field generated by the capacitive system;
    a skin electrostimulation system consisting of an electronic circuit comprising an electrostimulation generator which produces direct current and various types of square waves and half-waves with determined polarity, connected to one or more pairs of electrostimulating electrodes for delivering an electrostimulation to the patient's skin;
    a logic unit capable of managing and regulating the RF capacitive system and the electrical stimulation system;
    a handpiece comprising:
        a grip;
        a head having a concave or flat surface intended to come into contact with the patient's skin;
        the one or more shielded electrodes connected to the RF capacitive system placed in the central portion and/or on the edge of the surface of the handpiece head and coated with a dielectric intended to come into contact with the patient's skin; and
        the one or more pairs of electrostimulating electrodes connected to the electrostimulation system arranged so that the two electrodes of each pair are diametrically opposite each other in the central portion and/or on the edge of the surface of the handpiece head intended to come into contact with the patient's skin, wherein the one or more shielded electrodes and the one or more pairs of stimulating electrodes are configured to simultaneously and respectively apply, to the patient's skin, the electromagnetic field generated by the RF capacitive system and the skin electrostimulation generated by the electrostimulation system.

2. The device according to claim 1 comprising a vacuum generation system and the handpiece head being concave for application of a vacuum to the patient's skin.

3. The device according to claim 2, wherein said logic unit is a printed circuit provided with a microprocessor capable of managing and regulating the vacuum generation, the capacitive system and the electrical stimulation.

4. The device according to claim 2, wherein said vacuum generation system is a vacuum pump, or other device capable of creating a vacuum.

5. The device according to claim 2, wherein said handpiece is connected:

to the capacitive generator with a shielded coaxial cable;
to the electrical stimulation generator with a shielded multipolar cable;
to the vacuum generator with a pneumatic cable.

6. The device according to claim 1, wherein said alternating current power supply of the capacitive system is capable of generating a signal with a varying frequency from 0.3 to 1.5 MHz.

7. A method for stimulating cosmetic skin regeneration in a subject, said method comprising:

applying the device according to claim 1 to skin of the subject under conditions effective to simulate cosmetic skin regeneration.

8. The method according to claim 7 wherein:

values needed for the stimulating are automatically set by the logic unit once the reference handpiece is held by the patient and the device is activated; said applying comprising:

passing the handpiece directly over the skin surface of the patient, wherein said patient who simultaneously holds a reference handpiece intended to close the electromagnetic circuit and read the bio-feedback;

continuing said applying until the treated skin is slightly reddened, brighter and slightly warmer than the surrounding tissue.

9. The device according to claim 1, wherein said reference handpiece held by the patient consists of a metal or another electrically conductive material and is connected to the capacitive system by means of a monopolar cable.

10. The device according to claim 1, wherein the one or more shielded electrodes connected to the RF capacitive system are arranged in the central portion of the surface of the handpiece head intended to come into contact with the patient's skin while the two electrodes of each pairs of the one or more pairs of stimulating electrodes are arranged diametrically opposite to each other on the edge of surface of the handpiece head intended to come into contact with the patient's skin.

* * * * *